(12) United States Patent
Ho et al.

(10) Patent No.: US 8,530,420 B2
(45) Date of Patent: Sep. 10, 2013

(54) TREATMENT OF ARTHRITIS WITH PARATHYROID HORMONE

(75) Inventors: Mei-Ling Ho, Kaohsiung (TW);
Gwo-Jaw Wang, Kaohsiung (TW);
Je-Ken Chang, Kaohsiung (TW);
Yin-Chih Fu, Kaohsiung (TW);
Chung-Hwan Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 110 days.

(21) Appl. No.: 12/336,209

(22) Filed: Dec. 16, 2008

(65) Prior Publication Data
US 2010/0150997 A1    Jun. 17, 2010

(51) Int. Cl.
*A61K 38/29* (2006.01)
*A61K 38/22* (2006.01)
*A61K 38/17* (2006.01)
*A61K 38/16* (2006.01)

(52) U.S. Cl.
USPC ....... 514/11.8; 514/12.2; 514/16.6; 514/16.8; 514/21.3

(58) Field of Classification Search
None
See application file for complete search history.

(56) References Cited

U.S. PATENT DOCUMENTS

| | | | | |
|---|---|---|---|---|
| 5,457,092 | A | * | 10/1995 | Schluter et al. ................. 514/12 |
| 5,700,774 | A | * | 12/1997 | Hattersley et al. ............... 514/2 |
| 6,025,467 | A | * | 2/2000 | Fukuda et al. .................. 530/324 |
| 6,787,518 | B1 | | 9/2004 | Kato et al. |

FOREIGN PATENT DOCUMENTS

| | | |
|---|---|---|
| EP | 0 811 383 B1 | 5/2007 |
| WO | 2009/033666 A2 | 3/2009 |
| WO | 2010/045229 A2 | 4/2010 |

OTHER PUBLICATIONS

Ogawa et al., "Parathyroid Hormone Prevents Loss of Articular Cartilage in Tail-Suspended Rats", 47th Annual Meeting, Orthopaedic Research Society, Feb. 25-28, 2001, San Francisco, California.
Ho et al., "A novel terminal differentiation model of human articular chondrocytes in three-dimensional cultures mimicking chondrocytic changes in osteoarthritis", Cell Biology International 30 (2006) 288-294, Elsevier Ltd.
Kirsch et al., "Activation of annexin II and V expression, terminal differentiation, mineralization and apoptosis in human osteoarthritic cartilage", Osteoarthritis and Cartilage (2000) 8, 294-302.
Peat et al., "Knee pain and osteoarthritis in older adults: a review of community burden and current use of primary health care", Ann Rheum Dis 2001; 60:91-97.
Harvey et al., "Parathyroid Hormone-(1-34) Enhances Aggrecan Synthesis via an Insulin-like Growth Factor-I Pathway", Journal of Biological Chemistry, vol. 274, No. 33, pp. 23249-23255, Aug. 13, 1999.
Li et al., "Parathyroid hormone-related peptide (PTHrP) inhibits Runx2 expression through the PKA signaling pathway", Experimental Cell Research 299 (2004) 128-136, Elsevier Ltd.
Rabie et al., "PTHrP Regulates Chondrocyte Maturation in Condylar Cartilage", J Dent Res 82(8):627-631, 2003.
Vortkamp et al., "Regulation of Rate of Cartilage Differentiation by Indian Hedgehog and PTH-Related Protein", Science, vol. 273, Aug. 2, 1996.
Karaplis et al., "Role of PTHrP and PTH-1 Receptor in Endochondral Bone Development", Frontiers in Bioscience 3, d795-803, Aug. 1, 1998.
Weir et al., "Targeted overexpression of parathyroid hormone-related peptide in chondrocytes causes chondrodysplasia and delayed endochondral bone formation", Proc. Natl. Acad. Sci. USA, vol. 93, pp. 10240-10245, Sep. 1996.
Chung et al., "The parathyroid hormone/parathyroid hormone-related peptide receptor coordinates endochondral bone development by directly controlling chondrocyte differentiation", Proc. Natl. Acad. Sci. USA, vol. 95, pp. 13030-13035, Oct. 1998.

* cited by examiner

*Primary Examiner* — Elizabeth C Kemmerer
(74) *Attorney, Agent, or Firm* — WPAT, P.C.; Anthony King

(57) ABSTRACT

A method for treating and/or inhibiting arthritis is provided. The method includes administering an effective amount of a composition including a parathyroid hormone and a pharmaceutically acceptable carrier or salt to a subject with arthritis. Additionally, a method for inhibiting and/or rescuing terminal differentiation of cells is also provided.

19 Claims, 5 Drawing Sheets

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: An artificially synthesized forward primer
      nucleotide sequence

<400> SEQUENCE: 1
caacactgcc aacgtccaga t                                              21

<210> SEQ ID NO 2
<211> LENGTH: 24
<212> TYPE: DNA
<213> ORGANISM: Artificial
<220> FEATURE:
<223> OTHER INFORMATION: An artificially synthesized reverse primer
      nucleotide sequence

<400> SEQUENCE: 2
tcttgcagtg gtaggtgatg ttct                                           24

<210> SEQ ID NO 3
<211> LENGTH: 25
<212> TYPE: DNA
<213> ORGANISM: Artificial
<220> FEATURE:
<223> OTHER INFORMATION: An artificially synthesized forward primer
      nucleotide sequence

<400> SEQUENCE: 3
cagatttgag ctatcagacc aacaa                                          25

<210> SEQ ID NO 4
<211> LENGTH: 25
<212> TYPE: DNA
<213> ORGANISM: Artificial
<220> FEATURE:
<223> OTHER INFORMATION: An artificially synthesized reverse primer
      nucleotide sequence

<400> SEQUENCE: 4
aaattcaaga gaggcttcac atacg                                          25

<210> SEQ ID NO 5
<211> LENGTH: 23
<212> TYPE: DNA
<213> ORGANISM: Artificial
<220> FEATURE:
<223> OTHER INFORMATION: An artificially synthesized forward primer
      nucleotide sequence

<400> SEQUENCE: 5
tctcctctga cttcaacagc gac                                            23

<210> SEQ ID NO 6
<211> LENGTH: 22
```

```
<212> TYPE: DNA
<213> ORGANISM: Artificial
<220> FEATURE:
<223> OTHER INFORMATION: An artificially synthesized reverse primer
      nucleotide sequence

<400> SEQUENCE: 6
ccctgttgct gtagccaaat tc                                              22

<210> SEQ ID NO 7
<211> LENGTH: 22
<212> TYPE: DNA
<213> ORGANISM: Artificial
<220> FEATURE:
<223> OTHER INFORMATION: An artificially synthesized forward primer
      nucleotide sequence

<400> SEQUENCE: 7
aacttccaga ccattggctt ga                                              22

<210> SEQ ID NO 8
<211> LENGTH: 17
<212> TYPE: DNA
<213> ORGANISM: Artificial
<220> FEATURE:
<223> OTHER INFORMATION: An artificially synthesized reverse primer
      nucleotide sequence

<400> SEQUENCE: 8
ttgccgcgtg tcgtgtt                                                    17
```

TREATMENT OF ARTHRITIS WITH PARATHYROID HORMONE

BACKGROUND OF THE INVENTION

1. Field of the Invention

The present invention relates to a treatment of arthritis, and in particular relates to a method for treating osteoarthritis by parathyroid hormone.

2. Description of the Related Art

Arthritis is a group of conditions involving damage to the joints of the body. Arthritis is the leading cause of disability in people older than fifty-five years old. The most common form of arthritis, osteoarthritis is a result of trauma to the joint, infection of the joint, or age.

OA is a clinical syndrome in which low-grade inflammation results in pain in the joints, caused by abnormal wearing of the cartilage that covers and acts as a cushion inside joints and destruction or decrease of synovial fluid that lubricates those joints. As the bone surfaces become less well protected by cartilage, the patient experiences pain upon bearing weight, including walking and standing. Due to decreased movement because of the pain, regional muscles may atrophy, and ligaments may become more lax.

It has been reported that phenotypic changes for OA chondrocytes are similar to those in epiphyseal growth plates, wherein chondrocytes undergo terminal differentiation, hypertrophy, mineral deposition and eventually apoptosis (Arthritis Rheum 1998; 41(2):284-9; Ann Rheum Dis 2000; 59(12):959-65; Osteoarthritis Cartilage 2000; 8(4):294-302). The OA chondrocytes express the marker proteins of hypertrophic chondrocytes, annexins, alkaline phosphatase and collagen type X (Col X), but eliminate the expression of collagen type II (Col II).

OA affects nearly 21 million people in the United States, accounting for 25% of visits to primary care physicians, and half of all NSAID (Non-Steroidal Anti-Inflammatory Drugs) prescriptions. It is estimated that 80% of the population will have radiographic evidence of OA by age 65, although only 60% of those will be symptomatic.

Thus, to treat arthritis, particularly osteoarthritis, methods and compositions for suppressing and inhibiting terminal differentiation, hypertrophy, mineral deposition and apoptosis are necessarily required.

BRIEF SUMMARY OF THE INVENTION

The present invention provides a method for inhibiting and/or rescuing terminal differentiation of cells, comprising administering an effective amount of a composition comprising a parathyroid hormone and a pharmaceutically acceptable carrier or salt to the cells.

The present invention further provides a method for treating and/or inhibiting arthritis, comprising administering an effective amount of a composition comprising a parathyroid hormone and a pharmaceutically acceptable carrier or salt to a subject with arthritis.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
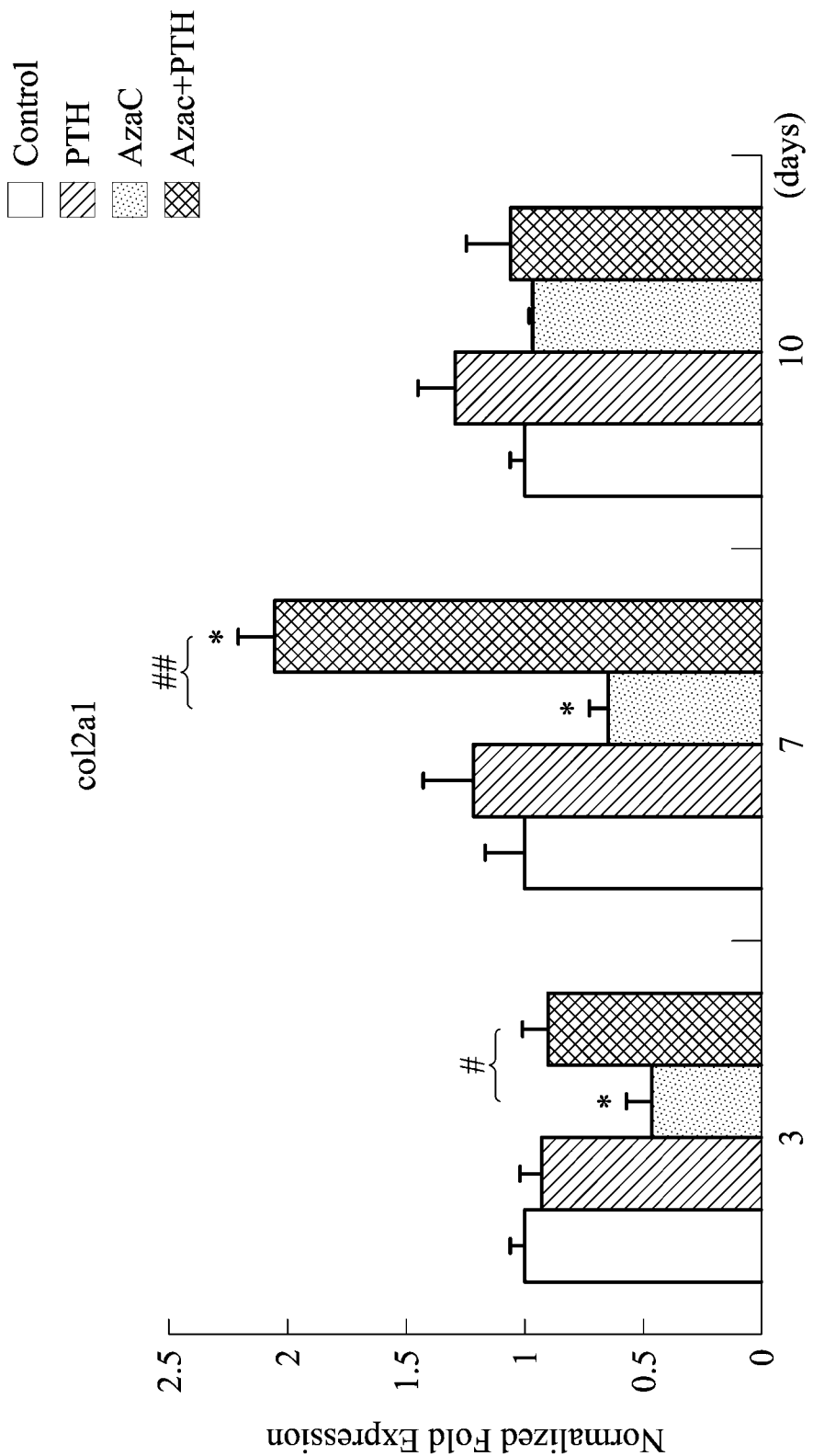
FIG. 1A shows the PTH treatment rescuing the AzaC-induced suppression of col2a1 mRNA.

The following description is of the best-contemplated mode of carrying out the invention. This description is made for the purpose of illustrating the general principles of the invention and should not be taken in a limiting sense. The scope of the invention is best determined by reference to the appended claims.

In one embodiment, the present invention provides a method for inhibiting and/or rescuing terminal differentiation of cells. The method comprises administering an effective amount of a composition comprising a parathyroid hormone and a pharmaceutically acceptable carrier or salt to the cell.

The term "parathyroid hormone (PTH)" of the present invention refers to the parathyroid hormone and its derivatives. Parathyroid hormone used in the present invention may occur in various forms such as PTH of a native type, PTH produced by genetic engineering techniques, or PTH synthesized chemically. Examples of PTH derivatives are partial peptides of the PTH as defined above, the constituent amino acids of the PTH of partial peptides thereof which may be partly replaced by other amino acids, the constituent amino acids of the PTH or partial peptides thereof which may be partly depleted, as well as peptides that have at least amino acid added to the PTH or partial peptides thereof. Note that the peptides as PTH derivatives may have similar activities to the PTH itself. Examples of partial peptides of PTH include human PTH(1-34), human PTH(1-64), human PTH(35-84) and bovine PTH(1-34). PTH(1-34) refers to a partial peptide of PTH that is composed of 34 amino acids as counted from the N terminus of PTH. In the present invention, PTH(1-34) is preferable.

The cells of the present invention comprising a chondrocyte, and preferably, an articular chondrocyte. Chondrocytes are the only cells found in cartilage. They produce and maintain the cartilaginous matrix, which consists mainly of collagen and proteoglycans. Chondrocytes can be obtained, for example, from normal mature cartilage tissue. Chondrocytes can be within a mammal.

The term "terminal differentiation" as used herein, refers to the final differentiation of a cell into a mature, fully differentiated cell.

The method of the invention can reverse the change of mRNA expression of collagen type IIα1 (col2a1), collagen type Xα1 (col10a1), and alkaline phosphatase (ALP) genes in a cell, preferably, articular chondrocyte. A PTH treatment can rescue the AzaC-induced terminal differentiation in articular chondrocytes. In an AzaC-induced terminal differentiation model, the PTH treatment not only rescues the AzaC-induced Col II suppression but further increases col2a1 mRNA expression. The elevation of mRNA expressions of col10a1 and ALP, and apoptosis induced by AzaC are also suppressed by PTH treatment.

After the PTH treatment, the expression of col2a1 showed an increase of at least 40%, preferably, about 40-60%, more preferably, about 50-60% compared to a non-PTH treatment. The expression of col10a1 showed a decrease of at least 1 fold, preferably about 1-4 folds, more preferably about 2-3 folds compared to a non-PTH treatment. The expression of ALP showed a decrease of at least 4 folds, preferably 4-10 folds, more preferably 5-9 folds compared to a non-PTH treatment. Additionally, the method of the invention can markedly suppress apoptosis of chondrocytes. After the PTH treatment, the apoptosis of chondrocytes was at least 1 fold, preferably about 1-2 folds lower than that without the PTH treatment.

In another embodiment, the present invention further provides a method for treating and/or inhibiting arthritis. The method comprises administering an effective amount of a composition comprising a parathyroid hormone and a pharmaceutically acceptable carrier or salt to a subject with arthritis to reduce the symptom of arthritis.

The term "arthritis" refers to any particular disease characterized by joint inflammation, although the etiology of the inflammation may differ in various conditions. Relatively common arthritic diseases include rheumatoid arthritis, juvenile arthritis, ankylosing spondylitis, psoriatic arthritis and osteoarthritis, preferably, osteoarthritis.

The "subject" of the invention refers to human or non-human mammal, e.g. a dog, a cat, a mouse, a rat, a cow, a sheep, a pig, a goat, or a primate, and expressly includes laboratory mammals, livestock, and domestic mammals. In one embodiment, the mammal may be a human; in others, the mammal may be a rodent, such as a mouse or a rat. In another embodiment, the subject is an animal model (e.g., a transgenic mouse model). Alternatively, the subject is an arthritis preferably, osteoarthritis patient.

The composition of the invention can be administered in combination with a second agent, including an organic bisphosphonate, a chemotherapeutic agent, a radiopharmaceutical agent, a TNF-alpha antagonist, a non-steroid anti-inflammation drug, a steroid, an anti-oxidant agent, an angiogenesis inhibitor, a matrix metalloproteinase inhibitor, a vitamin, a selective estrogen receptor modulator (SERM), an estrogen-progestin, an androgen, a calcitonin, an antibiotics, a cathepsin K inhibitor, a statin, an integrin receptor antagonist, an osteoblast anabolic agent, or a selective serotonin reuptake inhibitor, or mixtures thereof, for systemically or topically simultaneous, separate or sequential use. In the present invention, the second agent can be provided before, after, or at the same time as the parathyroid hormone.

The method can reduce the frequency and severity of osteoarthritis symptoms, rescue the papain-induced glycosaminoglycan (GAG) and collagen type II (Col II) decrease, and suppress the expression of collagen type X (Col X) in cartilage of the arthritis patients. In the papain-induced OA model of rat knees, the PTH treatment for 1-3 weeks can attenuate the decreases of GAG and Col II in cartilage. Furthermore, the PTH treatment for 5 weeks can rescue the expression of GAG and Col II, and also noticeably suppress Col X expression and apoptosis of chondrocytes that are caused by OA-induction.

Symptoms of osteoarthritis include, but are not limited to, pain (including joint pain), stiffness, limited joint movement, swelling, and bony enlargement. These symptoms may manifest themselves in various parts of a patient such as, for example, a hip, a knee, a spine, hands, or any other joints in the body. Furthermore, these symptoms may manifest during certain activities such as bending, kneeling, climbing stairs, running, rowing, and other strong or extended physical exertion, pain and stiffness in a joint during or after use, or after a period of inactivity, or any combination thereof. In addition, the symptom may be related to weather, such as discomfort in a joint before or during a change in the weather (a drop in barometric pressure).

The composition can be administered orally, intraarticularly, intraperitoneally, intrathecally, intrarterially, intranasally, intraparenchymally, subcutaneously, intramuscularly, intravenously, dermally, intrarectally, or topically. In one implementation, the composition can be injected, e.g., into the cerebro-spinal fluid. In another implementation, the subject is a fetus, and the composition is administered to the subject in the uterus.

The composition for treatment is formulated to be compatible with the route of administration. The composition can be formulated as a powder, a tablet, a pill, a granule, a capsule, a lotion, a suspension, a liposome formulation, a nasosphere, a patch, a suppository, an enema, a drip infusion, or an injection solution.

A solution for parenteral, intradermal, or subcutaneous administration can include: a sterile diluent such as water, saline, glycerin, fixed oils, polyethylene glycols, propylene glycol, or other synthetic solvents; an antibacterial agent such as benzyl alcohol or methyl parabens; an antioxidant such as ascorbic acid or sodium bisulfite; a chelating agent; or a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Oral compositions include tablets, capsules, troches, suspensions, and solutions. Such compositions can be fashioned with an inert diluent or an edible carrier. Capsules are made by combining an appropriate diluent with the compound and filling the capsule with the mixture. Common diluents are starches such as powdered cellulose, or sugars such as sucrose, fructose, or manitol. Tablets are made by wet or dry granulation or by compression. In addition to the desired compound, compositions for tablets can include: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature.

An appropriate dosage of the compounds for treatment must be determined. An effective amount of an inhibitor is the amount or dose which is required to ameliorate a spinal muscular atrophy symptom in a subject. Determination of the amount or dose required to treat an individual subject is routine to one skilled in the art, e.g., a physician, pharmacist, or researcher. First, the toxicity and therapeutic efficacy of the compound, e.g., EIPA, is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios are greater than about 2, 5, 10, 50, or 100. Compounds, formulations, and methods of administration with high therapeutic indices can be determined; as such treatments have little toxicity at dosages which provide high efficacy. Compounds with toxic or undesirable side effects can be used, if means are available to deliver the compound to the affected tissue, i.e., the spinal motor neurons and brain-stem neurons, while minimizing damage to unaffected tissue.

EXAMPLES

Example 1

Effect of PTH (1-34) on col2a1, col10a1, and ALP Gene Expression

First, human articular chondrocyte cultures were established. Briefly, normal human articular cartilage (KMU-AC) was isolated from fresh cadaver-knees of a 23-year-old Asian male, which were supplied by the Hospital of Kaohsiung Medical University. The cartilage was minced and sequentially digested by hyaluronidase (0.5 mg/ml), pronase (1 mg/ml) and collagenase (1 mg/ml), and isolated chondrocytes were encapsulated in alginate beads as described in Cell Biol Int 2006; 30(3):288-94, and J Rheumatol 2002; 29(4):772-82. Every 15 beads were cultured in 5 ml of culture medium per well in a 6-well plate. The culture medium was the DMEM containing 100 mg/ml of ascorbic acid, nonessential amino acids, penicillin/streptomycin, 1% ITS, and 10% fetal bovine serum. The beads were cultured for 7 days at 37° C. in a humidified 5% $CO_2$ incubator and the culture medium was changed every 3 days.

Next, the cultures were treated with 15 μg/ml of 5-azacytidine (AzaC) (Sigma, St Louis, Mo., USA) for 48 hours to induce terminal differentiation of chondrocytes as described in Cell Biol Int 2006; 30(3):288-94. After AzaC-induction, the cultures were then treated with a medium with or without 10 nM PTH(1-34) (Sigma, St Louis, Mo., USA) for 3, 7 or 10 days. In the control group, the cultures were not treated with AzaC-induction and PTH(1-34). In the AzaC group, the cultures were treated with AzaC, but without PTH (1-34). In the AzaC+PTH group, the cultures were treated with both AzaC-induction and PTH(1-34). In the PTH group, the cultures were treated with PTH (1-34) but without AzaC. The cells from all the groups were harvested at time points of the PTH treatment (following AzaC-induction) for 3, 7 or 10 days. Chondrocytes were released from alginate beads by dissolving the beads in a 0.9% NaCl solution containing 0.05M $Na_2$ citrate and 0.03M $Na_2$ EDTA at pH 7.4. Cells were collected for each experiment by a low-speed centrifugation at 1500 rpm for 5 min.

Then, total RNA was isolated from chondrocytes by using the RNeasy mini kit (Qiagen, Valencia, Calif., USA). The first strand cDNA was converted from 1 μg of RNA by using the Advantage RT-for-PCR kit (Clontech, Palo Alto, Calif., USA). Expressions of the mRNA of collagen type IIα1 and collagen type Xα1 and alkaline phosphatase (ALP) were measured by quantitative real-time PCR in the Bio-Rad iQ5 real-time PCR detection system (Bio-Rad, Hercules, Calif., USA) using the iQ™ SYBR® green supermix (Bio-Rad, Hercules, Calif., USA). Reactions were performed in a 25-μl mixture containing cDNA, specific primers of each gene and the iQ™ SYBR® green supermix. The cycling conditions were as follows: for collagen type IIα1 (col2a1), collagen type Xα1 (col10a1) and glyceraldehyde-3-phosphate dehydrogenase (GAPDH), cycling conditions were 1 cycle at 95° C. for 3 min, followed by 40 cycles of 95° C. for 10 sec, 61° C. for 30 sec and 55° C. for 1 min; for ALP, cycling conditions was 1 cycle at 95° C. for 3 min, followed by 40 cycles of 95° C. for 10 sec, 65° C. for 30 sec and 55° C. for 1 min. Primer sequences were as follows: (i) Collagen type IIα1 (81 bp product): Forward primer: 5'-CAA CAC TGC CAA CGT CCA GAT-3', designated as SEQ ID NO:1; Reverse primer: 5'-TCT TGC AGT GGT AGG TGA TGT TCT-3', designated as SEQ ID NO:2. (ii) Collagen type Xα1 (85 bp product): Forward primer: 5'-CAG ATT TGA GCT ATC AGA CCA ACA A-3', designated as SEQ ID NO:3; Reverse primer: 5'-AAA TTC AAG AGA GGC TTC ACA TAC designated as SEQ ID NO:4. (iii) GAPDH (126 bp product): Forward primer: 5'-TCT CCT CTG ACT TCA ACA GCG AC-3', designated as SEQ ID NO:5; Reverse primer: 5'-CCC TGT TGC TGT AGC CAA ATT C-3', designated as SEQ ID NO:6. (iv) Alkaline phosphatase (64 bp product): Forward primer: 5'-AAC TTC CAG ACC ATT GGC TTG A-3', designated as SEQ ID NO:7; Reverse primer: 5'-TTG CCG CGT GTC GTG TT-3', designated as SEQ ID NO:8.

The specific PCR products were detected by the fluorescence of SYBR Green, the double stranded DNA binding dye (Biotechniques 1998; 24(6):954-8, 960, 962). The relative mRNA expression level was calculated from the threshold cycle (Ct) value of each PCR product and normalized with that of the GAPDH by using the comparative Ct method (Methods 2001; 25(4):402-8). The relative quantity of the expression of each gene from the control cells on day 3 after AzC-induction was set to 100%, and all the others were transformed to a percentage change to the base. After the PCR reaction, a dissociation (melting) curve was generated to check the specificity of the PCR reaction. All the PCR amplifications were performed in triplicate, and experiments were repeated at least 3 times.

Figure 1B:
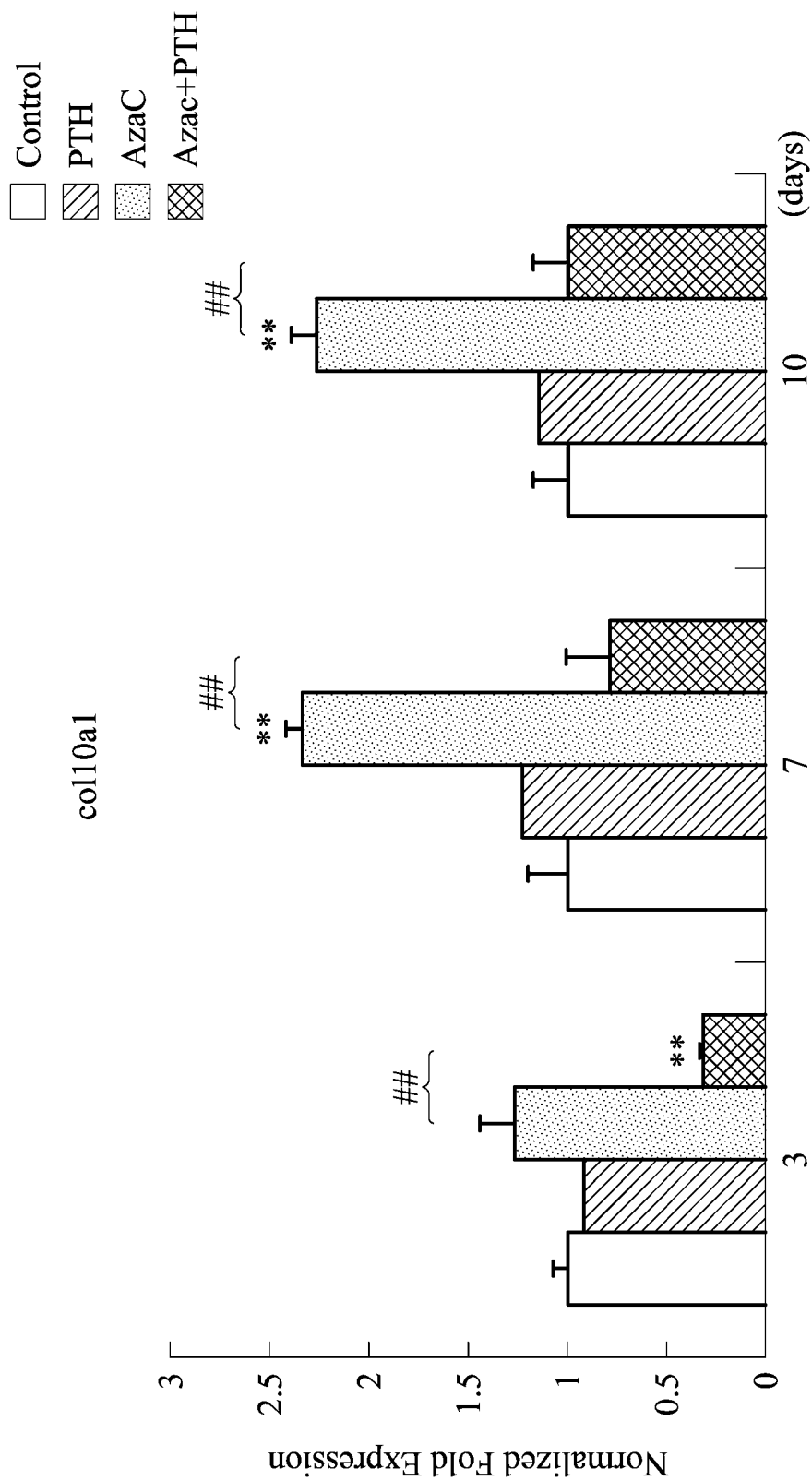
FIGS. 1B-1C show the PTH(1-34) suppressing the AzaC-induced mRNA expression of col2a1, col10a1 and ALP gene, respectively.
Figure 1C:
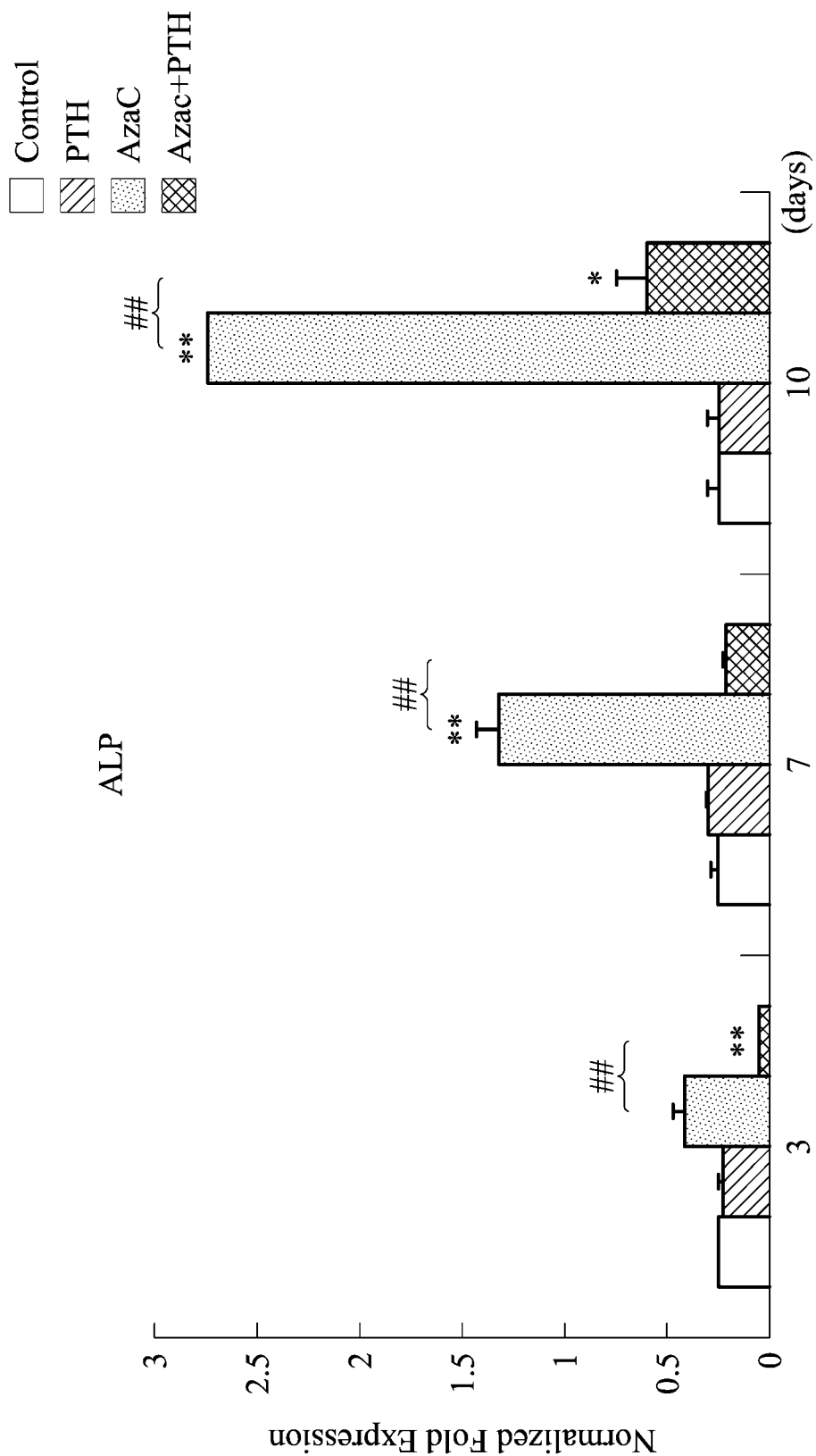

Referring to FIGS. 1A to 1C, In the AzaC group, the mRNA expression of col2a1 significantly decreased (56.7% of control, p<0.01) 3 days after AzaC-induction, and the col10a1 (2.4-2.5 folds of control) and ALP (5.3-8.3 folds of control) significantly increased (p<0.01) after 7 and 10 days of AzaC-induction. In the AzC+PTH group, the PTH(1-34) treatment reversed the AzaC-induced mRNA expression changes of col2a1, col10a1 and ALP. The col2a1 expression in AzaC+PTH cultures was significantly higher than that in AzaC cultures 3 days after the PTH treatment (p<0.05), and showed no significant difference from the control cultures, and 7 days after the PTH treatment, the col2a1 expression in AzaC+PTH cultures was higher than both the AzaC (p<0.01) and control (p<0.05) cultures (FIG. 1A). The mRNA expressions of col10a1 and ALP in the AzaC+PTH cultures were significantly eliminated after 3, 7 and 10 days of PTH(1-34) treatments in comparison to the AzaC cultures (p<0.01) (FIGS. 1B-C).

Example 2

Effect of PTH (1-34) on AzaC-Induced Apoptosis in Human Articular Chondrocytes

Apoptotic cells were measured by TUNEL (terminal deoxy-nucleotidyl transferase mediated dUTP nick end labeling) staining using the In Situ Cell Death Detection Kit, TMR red (Roche, Germany). According to the manufacturer's guidelines, cells were fixed with 4% of paraformaldehyde in a phosphate buffered solution (PBS) at a cell density of $1×10^6$/ml and incubated at room temperature for 10 min.

Figure 2:
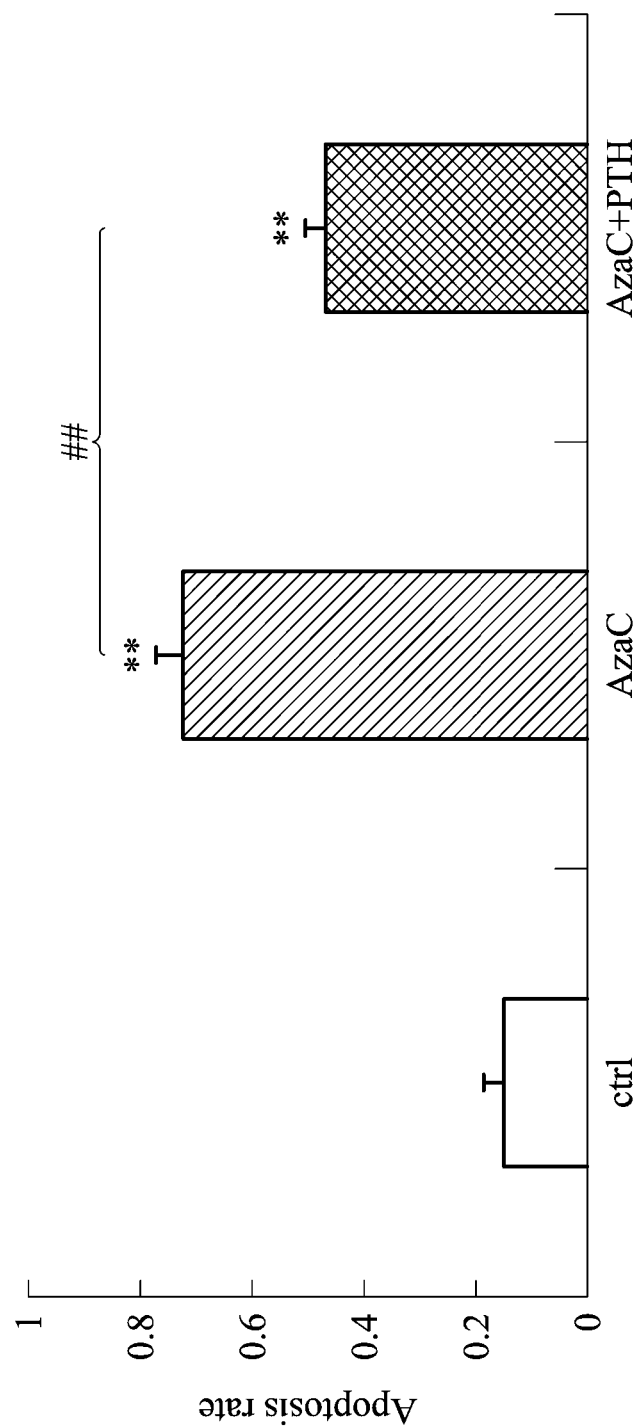
FIG. 2 shows the PTH(1-34) suppressing the AzaC-induced apoptotisis of articular chondrocytes.
Figure 3:
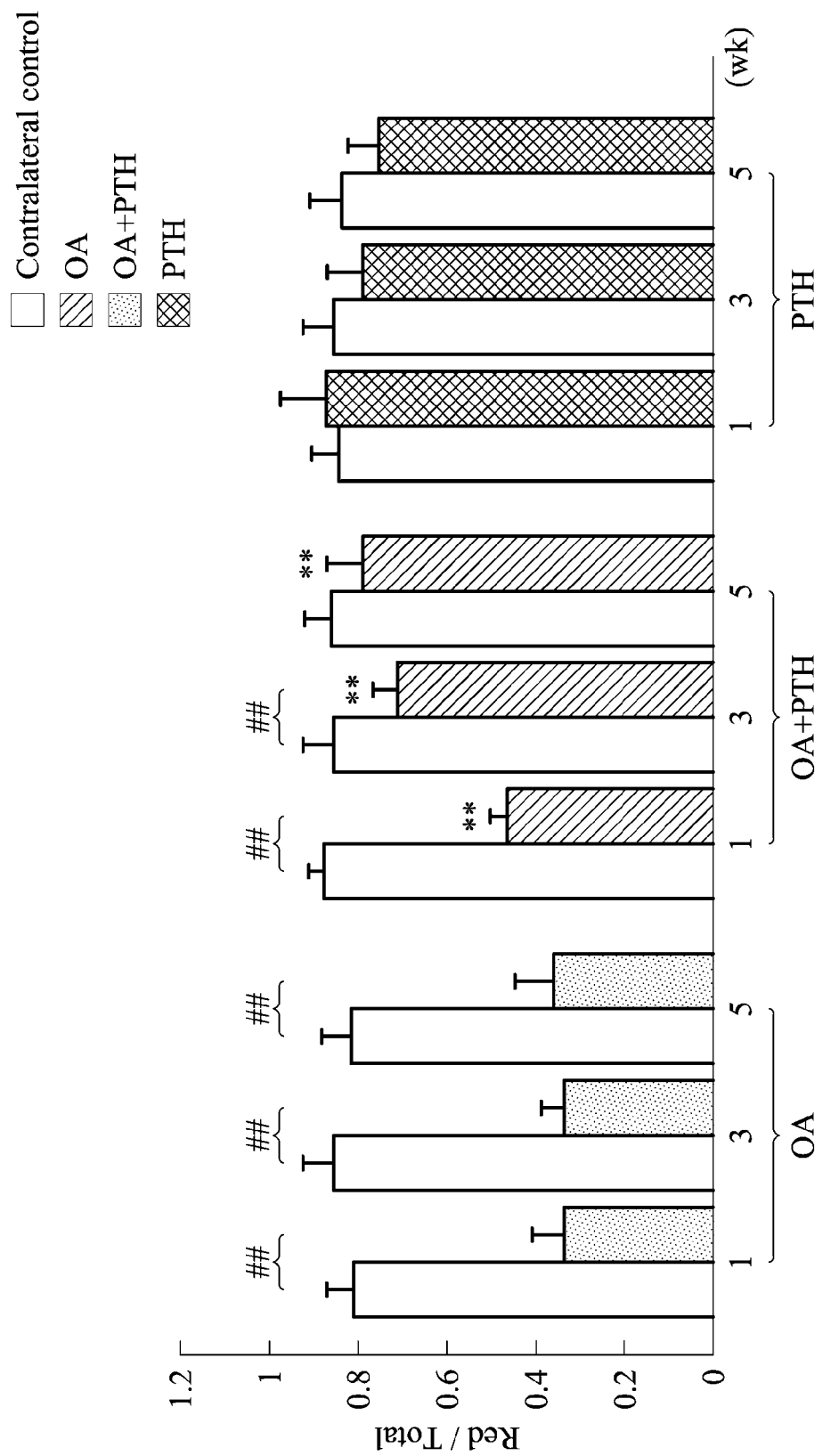
FIG. 3 show rescuing of the papain-induced GAG decrease in the cartilage 1.

Cells were then settled on a slide by centrifugation at a speed of 2000 rpm for 5 minutes by using a cytospin (Cytospin 3; Shandon, UK). Slides were rinsed twice with PBS, and cells were permeabilized by incubating in a permeabilization solution (0.1% Triton X-100 in 0.1% sodium citrate) for 2 minutes on ice. The TUNEL reaction mixture, containing terminal deoxy-nucleotidyl transferase and rhodamine (the labelling dye), was added to slides and incubated for 60 minutes at 37° C. in a humidified chamber in the dark. The reaction was stopped by a blocking buffer (0.1% TritonX-100/0.5% BSA in PBS). Cells were counter-stained by 4',6-diamidino-2-phenylindole (DAPI). Slides were observed on a fluorescence microscope with an excitation wavelength of 580 nm for rhodamine and 365 nm for DAPI. Cell nuclei were stained blue by DAPI, while only apoptotic cells were stained red by rhodamine. Stained cells were counted in 5 microscopic fields for each slide. Data were analyzed by using the Image-Pro Plus analysis software (Media Cybernetics, Sliver Spring, Md., USA). The ratio of red stained cells (apoptotic cells) to blue stained cells (total cells) was defined as the apoptotic rate of chondrocytes. Referring to FIG. 2, the apoptotic rate of articular chondrocytes at 14 days in the AzaC group was higher than that of control and AzaC+PTH groups. In comparison to the AzaC group, the apoptotic rate of the AzaC+PTH group was significantly lower (1.6-fold decrease, $p<0.01$).

Example 3

Effect of PTH(1-34) on Histological Appearance and Glycosaminoglycan Level in Normal and OA Articular Cartilage The animal experiment was approved by the Animal Care and Use Committee of the Kaohsiung Medical University. Fifty-four 12-week-old female Sprague-Dawley rats (body weight 250-300 g) were purchased from the BioLASCO Taiwan Co., Ltd. Center. Rats were classified into three groups: (1) OA group (n=18), (2) OA+PTH group (n=18), and PTH group (n=18). The left knee joint of each rat in all the 3 groups did not receive any treatment as the contralateral control. In the OA group, the right knees of rats were induced OA by intra-articular injection of 20 μl of 4% papain solution and 20 μl of 0.03 M cystein via the patellar tendon by using a 26-gauge needle at day 1, 4 and 7 of the experiment as disclosed in Nucl Med Commun 1996; 17(6):529-35. In the OA+PTH group, following OA-induction, the right knees of rats were intra-articularly injected with 40 μl of 10 nM PTH (1-34) every 3 days until sacrifice. In the PTH group, the same PTH (1-34) treatment was performed but without the previous OA-induction. Six rats of each group were sacrificed with an overdose of $CO_2$ inhalation at the end of the 1st, 3rd or 5th week of PTH (1-34) treatment. After sacrifice, the knees of rats were disarticulated, and patellae, femoral condyles and tibial plateaus were collected and fixed with 10% neutral buffered formalin prior to histological preparation. The samples were then decalcified in 10% formic acid/PBS. The decalcified tibia joints were paraffin embedded, and 5 μm microsections were prepared. The glycosaminoglycan (GAG) was stained with Safranin-O-Fast-Green (1% Safranin-O and counter-stained with 0.75% hematoxylin and then 1% fast green) (Sigma, St. Louis, Mo., USA). Localized Col II and Col X were immuno-stained. The representative histological appearances of the Safranin-O stained articular cartilages from the contralateral control of the OA group, as well as the OA, OA+PTH and PTH groups were analyzed. Referring to 3C, there was no significant difference in the ratio of Safranin-O stained area to total area (red/total) of the control cartilage in the OA, OA+PTH and PTH groups. The red/total ratio in cartilage of the OA group was significantly lower than that of the contralateral control cartilage at 1, 3 and 5 weeks OA-induction ($p<0.01$). The red/total ratio in cartilage of the OA+PTH group was also significantly lower than the contralateral control upon 1 and 3 weeks of the PTH treatment (following OA-induction) ($p<0.01$). However, no significant difference from the contralateral control was observed after 5-weeks of the PTH treatment. In comparing the PTH+OA group with the OA group, the red/total ratio in the OA+PTH was significantly higher than that of the OA group upon 1-, 3- and 5-week treatments of the PTH(1-34) ($p<0.01$). In the PTH group, there were no significant differences between the PTH and the contralateral control of each group at each time point of the PTH treatment. The results indicate that the PTH treatment increases the GAG level in the OA articular cartilage.

Example 4

Effect of PTH (1-34) on Immunolocalized Collagen Type II (A) and Collagen Type X (B) in Normal and OA Articular Cartilage The tibia joint sections of rats obtained from Example 3 were re-hydrated, and the endogenous peroxidase in tissues was blocked with 3% hydrogen peroxide. Samples were digested by enzymes for epitope retrieval prior to incubation with primary anti-bodies. The methods for enzyme digestion were modified from J Histochem Cytochem 2002; 50(8): 1049-58. The optimal condition of the enzyme digestion for Col II immuno-staining was with a mixture of 2.5% hyluronidase and 1 mg/ml pronase in the PBS (pH 7.4) (Sigma, St. Louis, Mo., USA) for 1 hour at 37° C., the optimal condition for Col X immuno-staining was with 0.1 U/ml chondroitinase ABC (Sigma, St. Louis, Mo., USA) for 1 hour and pepsin 1 mg/ml in tris-HCl (pH 2.0) for 15 minutes at 37° C. Sections were then blocked with fetal bovine serum for 1 hour, and were incubated with primary antibodies of Col II (mouse monoclonal antibody) (Chemicon International, Temecula, Calif., USA) and Col X (mouse monoclonal antibody) (1:100) (Sigma, St. Louis, Mo., USA) for 1 hour at room temperature. The $2^{nd}$ antibodies were incubated for 30 minutes by using the Biotinylated link (containing biotin labeled goat anti-rabbit and goat ant-mouse immunoglobulin) and the Streptavidin-HRP (streptavidin conjugated to horseradish peroxidase) (DAKO, Carpinteria, Calif., USA). Color was developed by a 3,3'-diaminobenzidine solution containing 0.01% hydrogen peroxide, resulting in brown staining. Finally, sections were counterstained with hematoxylin and observed on a microscope. In comparison to the contralateral control, immunolocalized Col II was noticeably eliminated in cartilage of the OA group at 3 and 5 weeks after OA-induction, and was more noticeable at 5 weeks after OA-induction. In the OA+PTH groups, the immunolocalized collagen type II was only slightly decreased upon a 3-week PTH(1-34) treatment (following OA-induction) in comparison to the contralatral control; however, upon a 6-week treatment of PTH(1-34), no obvious differences were observed between the OA+PTH and the contralatral control cartilages. The results indicate that the PTH treatment increases the collagen type II in the OA articular cartilage. Additionally, the immunolocalized Col X (stained brown) was found in hypertrophic chondrocytes of the OA cartilage, but was rarely found in the OA+PTH cartilages when the rats received 3 and 5 weeks of PTH(1-34) treatments. The results indicate that the PTH treatment noticeably suppresses the collagen type X in the OA articular cartilage. In addition, The result of TUNEL staining showed that lots of apoptotic cells (stained red) were found in the OA cartilage, while it was noticeably eliminated in the OA+PTH cartilage that received 3 and 5 weeks of the PTH(1-34) treatments.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for inhibiting and/or rescuing terminal differentiation of an articular chondrocyte, comprising administering a subject in need by intra-articular injecting an effective amount of a composition consisting essentially of a human PTH(1-34) or a bovine PTH(1-34), and a pharmaceutically acceptable carrier or salt to the articular chondrocyte.

2. The method as claimed in claim 1, wherein the human PTH (1-34) is used.

3. The method as claimed in claim 1, wherein the human PTH(1-34) or a bovine PTH(1-34) rescues the 5-azacytidine-induced col2a1 mRNA decrease in the articular chondrocyte.

4. The method as claimed in claim 1, wherein the human PTH(1-34) or a bovine PTH(1-34) suppresses the 5-azacytidine-induced col10a1 or ALP mRNA expression in the articular chondrocyte.

5. The method as claimed in claim 1, wherein the human PTH(1-34) or a bovine PTH(1-34) suppresses the apoptosis of the articular chondrocyte.

6. The method as claimed in claim 1, wherein the articular chondrocyte is within a mammal.

7. A method for increasing and/or preventing loss of glycosaminoglycan level and/or collagen type II, and/or suppressing collagen type X expression and/or apoptosis in articular cartilage, comprising administering a subject in need by intra-articular injecting an effective amount of a composition consisting essentially of a human PTH(1-34) or a bovine PTH(1-34), and a pharmaceutically acceptable carrier or salt to a subject with arthritis.

8. The method as claimed in claim 7, wherein the arthritis is osteoarthritis.

9. The method as claimed in claim 7, wherein the human PTH(1-34) is used.

10. A method for increasing and/or preventing loss of glycosaminoglycan level and/or collagen type II, and/or suppressing collagen type X expression and/or apoptosis in articular cartilage, comprising administering a subject in need by intra-articular injecting an effective amount of a composition consisting essentially of a human PTH(1-34) or a bovine PTH(1-34), and a second agent selected from the group consisting of an organic bisphosphonate, a chemotherapeutic agent, a radiopharmaceutical agent, a TNF-alpha antagonist, a non-steroid anti-inflammation drug, a steroid, an anti-oxidant agent, an angiogenesis inhibitor, a matrix metalloproteinase inhibitor, a vitamin, a selective estrogen receptor modulator (SERM), estrogen-progestin, an androgen, calcitonin, an antibiotics, a cathepsin K inhibitor, a statin, an integrin receptor antagonist, an osteoblast anabolic agent, a selective serotonin reuptake inhibitor, and mixtures thereof.

11. The method as claimed in claim 10, wherein the second agent is provided after the human PTH(1-34) or a bovine PTH(1-34).

12. The method as claimed in claim 10, wherein the second agent is provided before the human PTH(1-34) or a bovine PTH(1-34).

13. The method as claimed in claim 10, wherein the second agent is provided at the same time as the human PTH(1-34) or a bovine PTH(1-34).

14. The method as claimed in claim 7, wherein the composition is formulated as a powder, a suspension, a liposome formulation, a drip infusion, or an injection solution.

15. The method as claimed in claim 7, wherein the subject is a mammal.

16. The method as claimed in claim 7, wherein the human PTH(1-34) or a bovine PTH(1-34) rescues the papain-induced glysaminoglycan and Col II decrease in a cartilage of the subject.

17. The method as claimed in claim 7, wherein the human PTH(1-34) or a bovine PTH(1-34) suppresses the papain-induced Col X expression in a cartilage of the subject.

18. The method as claimed in claim 7, wherein the method reduces the frequency and severity of osteoarthritis symptoms.

19. The method as claimed in claim 18, wherein the symptoms comprise joint pain, joint stiffness, joint inflammation, or and lack of function from the affected joint.

* * * * *